(12) United States Patent  
Yao et al.

(10) Patent No.: US 6,730,033 B2  
(45) Date of Patent: May 4, 2004

(54) TWO DIMENSIONAL ARRAY AND METHODS FOR IMAGING IN THREE DIMENSIONS

(75) Inventors: Lin Xin Yao, Bellevue, WA (US); Todor Sheljaskow, Issaguale, WA (US)

(73) Assignee: Siemens Medical Systems, Inc., Malvern, PA (US)

( * ) Notice: Subject to any disclaimer, the term of this patent is extended or adjusted under 35 U.S.C. 154(b) by 16 days.

(21) Appl. No.: 10/147,423

(22) Filed: May 16, 2002

(65) Prior Publication Data

US 2003/0216645 A1 Nov. 20, 2003

(51) Int. Cl.[7] ............................................. A61B 8/00
(52) U.S. Cl. .................................................. 600/443
(58) Field of Search ............................ 600/407–471; 73/625, 626; 128/916, 899; 367/7, 11, 130, 138

(56) References Cited

U.S. PATENT DOCUMENTS

| | | |
|---|---|---|
| 5,690,113 A | 11/1997 | Sliwa, Jr. et al. |
| 5,764,596 A | 6/1998 | Hanafy et al. |
| 5,876,345 A | 3/1999 | Eaton et al. |
| 5,894,646 A | 4/1999 | Hanafy et al. |
| 6,014,473 A | 1/2000 | Hossack et al. |
| 6,043,589 A | 3/2000 | Hanafy |
| 6,045,508 A | 4/2000 | Hossack et al. |

Primary Examiner—Ali M. Imam

(57) ABSTRACT

A two-dimensional array allows rapid three-dimensional ultrasound scanning. A high volume-per-second scan rate using a limited number of system channels (e.g. 192, 256 or other number of channels) is provided by a transducer array without beamforming circuitry in the probe. A fan beam of acoustic energy is transmitted along a scan plane from transducer elements that extend lengthwise over a substantial portion of the lateral aperture. Rows of these long transmit elements are provided along the elevation aperture for electronic steering of the fan beam in the elevation dimension. One or more rows of smaller receive elements are used for forming beams each representing a scan line along the lateral dimension in response to each transmission of a fan beam. Elevation resolution is provided primarily from the elevationally spaced transmit elements and partially from two or more rows of laterally spaced receive elements. The lateral resolution is responsive to the lateral spacing of the receive elements.

28 Claims, 4 Drawing Sheets

TWO DIMENSIONAL ARRAY AND METHODS FOR IMAGING IN THREE DIMENSIONS

BACKGROUND

The present invention relates to transducer arrays for ultrasound imaging. In particular, two-dimensional transducer arrays for generating images representing two and three dimensions are provided.

Ultrasound imaging for echocardiography applications requires transducers with high volume-per-second rates for scanning. For real-time imaging of moving structures, 20 or more, such as 35, two or three-dimensional representations are generated each second.

Various transducers and associated beamformers have been provided for three-dimensional ultrasound imaging. Currently, mostly mechanical transducers are used. However, the associated imaging is not provided in real time and typically requires ECG gating. Two-dimensional transducer arrays for faster electronic/electronic steering and volume acquisition also have been provided. For example, sparse two-dimensional arrays or fully sampled two-dimensional arrays have been used. Sparse arrays provide poor contrast resolution. Further, the volume-per-second rates for scanning are limited by the speed of sound in the human body and the necessity of having a plurality of ultrasound beams in order to acquire the three-dimensional volume. Likewise fully sampled two-dimensional arrays are also limited by the speed of sound and the necessity of having a plurality of ultrasound beams and require expensive additional beamforming hardware for reducing the number of cables required. As other examples, arrays with beamforming capabilities within a probe or housing for the transducer array are provided. These arrays include walking or rotating aperture two-dimensional arrays, partial beamforming two-dimensional arrays using subarrays, and two-dimensional arrays with time division multiplexing. However, arrays with beamforming in a handle require expensive hardware and are restricted by the same speed of sound limitations.

Two-dimensional arrays repetitively generate transmit beams and responsive receive beams. The beams are electronically steered within the three-dimensional volume. Electronic steering requires a system channel for each of the elements used. Since the number of elements in a two-dimensional array is high, the number of channels required is high. More channels require a greater number of cables. Providing beamforming within the handle of the transducer array may reduce the number of cables required, but the required number of channels and hardware for sampling the two-dimensional array is still high.

Given a volume acquisition rate of 35 fully sampled volumes per second, receiving along four scan lines in response to each transmission, using a single transmit focus over a 90 degree field of view, and for imaging at 40 millimeters of depth, the volume acquisition is limited to about 2000 receive beams. Each transmission takes time. For the acquisition of three-dimensional volumes, the beam width is made larger to account for the limited number of beams while still scanning the whole volume. As a result, the three-dimensional volume is scanned with reduced lateral and elevation resolution. For example, a three-dimensional volume is scanned to a 40 millimeter depth using 44 beams for each scan plane with a −6 dB width of 2.9 millimeters for each beam. To increase the resolution, the volumes scanned per-second is decreased, allowing more beams to be used in the same sized volume. Real time three-dimensional imaging is sacrificed for per resolution.

BRIEF SUMMARY

The present invention is defined by the following claims, and nothing in this section should be taken as a limitation on those claims. By way of introduction, the preferred embodiments described below include a two-dimensional transducer array and methods for using the array for two and three-dimensional imaging. A high volume-per-second scan rate using a limited number of system channels (e.g. 192, 256 or other number of channels) is provided by a transducer array without beamforming circuitry in the probe. A fan beam of acoustic energy is transmitted along a scan plane from transducer elements that extend lengthwise over a substantial portion of the lateral aperture. Rows of these long transmit elements are provided along the elevation aperture for electronic steering of the fan beam in the elevation dimension. One or more rows of smaller receive elements are used for forming beams each representing a scan line along the lateral dimension in response to each transmission of a fan beam. Elevation resolution is provided primarily from the elevationally spaced transmit elements and partially from two or more rows of laterally spaced receive elements. The lateral resolution is responsive to the lateral spacing of the receive elements.

In a first aspect, a two-dimensional array for three-dimensional imaging is provided. A first row of the array has at least one first element. A second row of the array is provided adjacent the first row. The second row has at least two second elements. The first element is at least about twice as long in a lateral dimension as each of the second elements.

In a second aspect, an ultrasound system for three-dimensional scanning is provided. A transmit beamformer and a receive beamformer connect to a two-dimensional array of elements. At least a first subset of the elements are connectable with the transmit beamformer, and at least a second subset of the elements are connectable with the receive beamformer. The first subset of elements comprises a greater number of elevation spaced elements than lateral spaced elements, and the second subset of elements comprises a greater number of lateral spaced elements than elevation spaced elements.

In a third aspect, a method for three-dimensional scanning with a two-dimensional array is provided. Acoustic energy is electronically focused in an elevation dimension and transmitted. The acoustic energy has a uniform field in a lateral dimension. At least two beams are electronically focused in the lateral dimension and formed in response to the transmission.

Further aspects and advantages of the invention are discussed below in conjunction with the preferred embodiments.

BRIEF DESCRIPTION OF SEVERAL VIEWS OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE PREFERRED EMBODIMENTS

A two-dimensional array and beamformer system for real time three-dimensional imaging is provided. For example, echocardiography using 192, 256 or other limited number of system channels and a high volume-per-second scanning rate is provided. A curved two-dimensional array allows real time three-dimensional imaging with the limited number of channels without beamforming circuitry in the handle. The array includes transmit elements elongated along a lateral dimension to transmit a fan beam of acoustic energy. A plurality of elevationally spaced rows of the elongated transmit elements provide elevation focusing. One or more rows of multiple elements along a lateral dimension allow for lateral focusing on receive with parallel beamforming. This two-dimensional array reduces the required number transmit and receive cycles.

Figure 1:
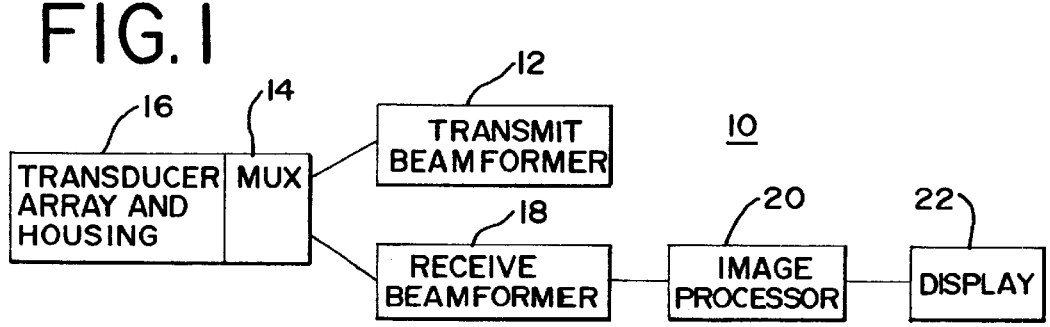
FIG. 1 is a block diagram of one embodiment of an ultrasound system for three-dimensional imaging.

FIG. 1 shows a system 10 of one embodiment for three-dimensional imaging. The system 10 includes a transmit beamformer 12, a multiplexer 14, a transducer array and housing 16, a receive beamformer 18, an image processor 20, and a display 22. Additional, different or fewer components may be provided. The system 10 is operable to scan a three-dimensional volume and generate images representing the three-dimensional volume in real time, such as providing 20 or more images per second.

The transmit beamformer 12 comprises analog and/or digital components for generating a plurality of transmit waveforms on system channels. For example, the transmit beamformer 12 includes: one or more waveform generators for generating unipolar, bipolar, sinusoidal, sinusoidal with Gaussian or other non-uniform envelope, or other transmit waveforms; a plurality of delays for delaying the waveform of one channel relative to waveforms of other channels; and a plurality of variable or programmable amplifiers for applying apodization as a function of the channel. In one embodiment, the transmit beamformer 12 generates frequency coded or other coded transmit waveforms. The transmit beamformer 12 includes a channel for generating a transmit waveform for each of the transducer elements used in any given transmit aperture. For example, the transmit beamformer 12 includes 16, 32, 192, 256 or other number of transmit channels. Using the relative delays and apodization, the transmit beamformer 12 causes acoustic energy transmitted from the transducer array 16 to be focused in an elevation dimension along a scan plane. No, some or minimal focusing may be provided along a lateral dimension within the scan plane. For example, the transmit beamformer 12 transmits a fan beam or uniform field of acoustic energy along all of or a portion of a field of view or scan plane.

The multiplexer 14 comprises one or more analog or digital switches for routing transmit waveforms from the transmit beamformer 12 to the transducer array 16, and routing receive signals from the transducer array 16 to the receive beamformer 18. The multiplexer 15 operates at high voltages associated with transmission of ultrasound. In one embodiment, the multiplexer 14 interconnects fewer than all of the elements of the transducer array 16 to the transmit beamformer 12 or the receive beamformer 18. In other alternative embodiments, the multiplexer 14 is optional, allowing direct connection of the transmit beamformer 12 to transmit elements of the transducer array 16 and direct connection of the receive beamformer 18 to separate receive elements of the transducer array 16. In yet other embodiments, only a subset of the elements of the transducer array 16 connect with the multiplexer 14 and the remaining elements connect directly to the transmit beamformer 12 or the receive beamformer 18.

The receive beamformer 18 comprises analog and/or digital components for forming data or beams representing one or more scan lines in response to reception of acoustic energy. For example, the receive beamformer 18 comprises delays and amplifiers for applying focusing and apodization across a plurality of receive system channels and a summer for summing the delayed and apodized information. Radio frequency or other received electrical signals from the transducer array 16 are provided to the receive beamformer 18 for generating beams of data. In one embodiment, the receive beamformer 18 includes components for generating two or more beams of data in response to a single transmission. For example, separate delays, amplifiers and summers are provided simultaneously for forming beams representing different scan lines within a two-dimensional field of view. The receive beamformer 18 electronically focuses the received information in two dimensions such as a lateral dimension and a range or depth dimension. In one embodiment, the receive beamformer 18 includes components for forming a large number of received beams in response to transmission of a single fan beam. For example, tens or hundreds of receive beams are simultaneously or substantially simultaneously generated in response to one fan beam transmission. In alternative embodiments, the receive beamformer 18 includes a memory for storing the radio frequency data for each of the receive system channels. Receive beams are then sequentially formed. In yet other alternative embodiments, a combination of sequential and simultaneous beam formation is provided. In yet another alternative embodiment, the receive beamformer 18 comprises a processor or other digital or analog circuitry for forming beams by application of a Fast Fourier transform algorithm rather than delay and summation as discussed above.

The image processor 20 receives the formed beam information for generating an image. In one embodiment, the image processor 20 comprises ultrasound B-mode and/or Doppler detectors. The image processor 20 spatially coordinates the receive beams for three-dimensional image rendering. For example, using surface extraction, maximum projection, minimum projection, other projection, or other three-dimensional rendering algorithms, an image is generated for display on the display 22. The display includes intensity information representing tissue or B-mode detected information and/or color information representing velocity, energy or variance of moving fluid or tissues. Other detected information may be used, such as a detected loss of correlation associated with contrast agent. The receive beamformer 18 outputs data at a rate sufficient to allow generation of 20 or greater, such as 35, images a second on the display 22. The system 10 scans a three-dimensional field of view of a patient quickly enough to allow real time echocardiography imaging.

The configuration of the transducer array 16 allows for rapid three-dimensional scanning. The transducer array 16 includes a housing adapted for use externally or internally to a patient. For example, the housing includes a plastic or other coating with an acoustic window adjacent to an array of transducer elements.

Figure 2:
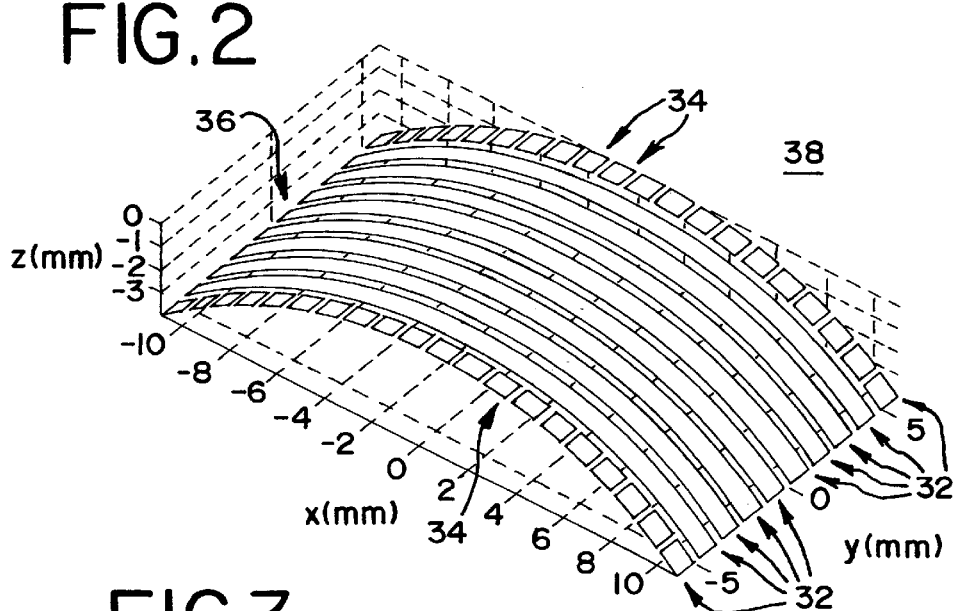
FIG. 2 is a graphical representation of one embodiment of a two dimensional array of elements.

FIG. 2 shows one embodiment of an array of elements 30. The array 30 includes a plurality of elements 34, 36. The elements 34, 36 comprise piezoelectric material, microelectromechanical devices, or other materials for transducing between acoustic and electric energy. The array 30 comprises a two-dimensional array, such as a plurality of elements along an X or lateral dimension and a plurality of elements along a Y or elevation dimension. As shown in FIG. 2, the array 30 comprises a curved array, such as curving along the lateral or X dimension in a depth or range (Z) dimension. The curvature is selected to allow transmission in a likely field of view and provide as many as possible elements 34 along a lateral dimension for receive beam formation.

The elements 34, 36 are arranged in a plurality of elevationally spaced rows 32. The rows 32 are parallel. In alternative embodiments, the rows 32 are non-parallel. As shown in FIG. 2, the rows 32 are straight or do not curve in the lateral and elevation directions. In alternative embodiments, the rows 32 curve in dimensions other than or in addition to the range dimension. In yet other embodiments, the array 30 is flat without any curvature.

As shown in FIG. 2, two of the rows 32 include small elements 34. The small elements 34 are about 0.5 to 1 wavelength of a center frequency of the array 30 in the lateral dimension. A similar or different width is provided along the elevation dimension. A plurality of the small elements 34 are spaced within a row 32 along the lateral dimension. For example, 16 or more small elements 34 extend along the lateral aperture or extent of the array 30. In one embodiment, 64 or more small elements 34 are provided in each row 32 used for the small elements 34. As shown in FIG. 2, only two rows comprise small elements 34. In alternative embodiments, one, three or more of the elevationally spaced rows 32 include small elements 34. For example, ten or more rows 32 extend along the elevation aperture of the array 30. A greater number of smaller elements 34 are provided along the lateral dimension than along the elevation dimension. For example, FIG. 2 shows two elevationally spaced rows of twenty laterally spaced smaller elements 34 each.

The small elements 34 are used as receive elements. Each receive element connects with a receive system channel to pass radio frequency signals to the receive beamformer 18. The receive elements are used for two-dimensional receive focusing and steering. The receive beamformer 18 forms beams within a two-dimensional scan plane by steering electronically. The small elements 34 allow for lateral steering with a good lateral resolution.

In one embodiment, the number of small elements 34 corresponds to the number of receive channels. For example, half of the receive channels connect to small elements 34 on one elevation edge of the array 30 and the other half of the receive system channels connect to small elements 34 on the other elevation edge of the array 30. Accordingly, the multiplexer 16 for switching between elements is not needed. In alternative embodiments, the multiplexer 16 allows for more possible receive elements than receive system channels.

Figure 3:
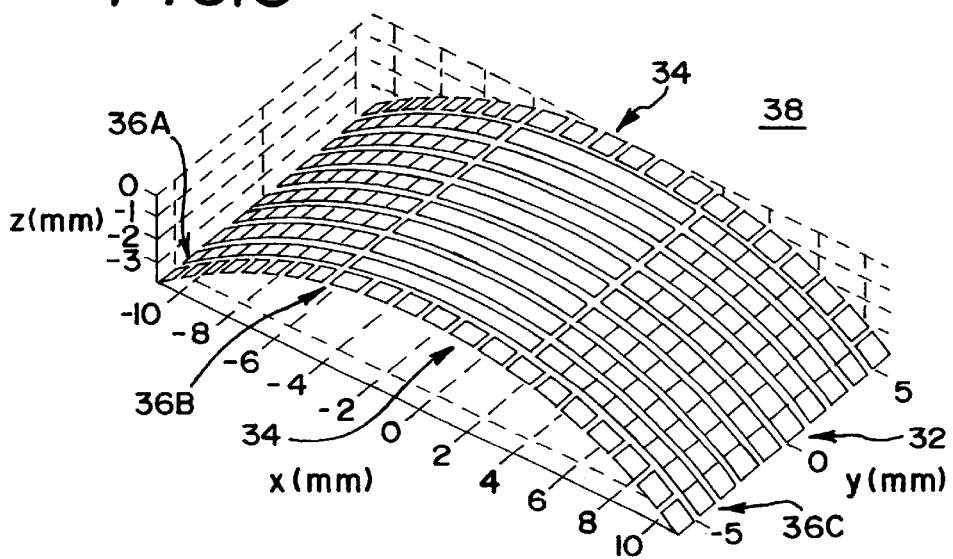
FIGS. 3–6 are graphical representations of other embodiments of two-dimensional arrays of elements.

The larger elements 36 are at least twice as long as the smaller elements 34 in the lateral dimension. As shown in FIG. 2, each of the larger elements 36 extends as a single element across the lateral aperture of the array 30. The elevational width of each of the larger elements 36 is the same as the elevational width of the smaller elements 34, but may be larger or smaller. In other embodiments, the large elements 36 are subdivided or divided into a plurality of laterally spaced elements. FIG. 3 shows positioning three laterally spaced larger elements 36A, 36B and 36C along each of the rows 32 associated with these larger elements 36. The lateral aperture may be divided by half, by a third, by a fourth, by an eighth or other number of large elements 36. In one embodiment, fewer than nine larger elements 36A, 36B, 36C are used in any row 32, but more than eight large elements 36 may be used in a row 32. As shown in FIG. 3, the large elements 36A, 36B, 36C are still at least twice as long in a lateral dimension as any one of the smaller elements 34.

In alternative embodiments, each of the larger elements 36 is further subdivided to be a same or similar size as the smaller elements 34. Accordingly, the array can be used for standard two-dimensional imaging or full array sampled three-dimensional imaging. For operation as a one-dimensional curved array, an acoustic lens may be added on top of the array or to the housing for fixed focusing in the elevation direction. For transmission of a fan beam as discussed herein, the smaller elements are switched together to act as a larger element 36 with high voltage multiplexers. As used herein, an element that is larger than another element is larger through electrical connection of smaller elements or larger through physical characteristics, such as location of kerfing or other physical separation between elements.

The large elements 36 are provided in each of a plurality of elevationally spaced rows 32. For example, 2, 3, 16, 32, more, or any other number of rows 32 with large elements 36 may be provided. In one embodiment, a greater number of large elements 36 are provided across an elevation aperture than across the lateral aperture. For example, FIG. 3 shows eight large elements 36A, 36B, 36C across an elevation aperture and three across a lateral aperture. As another example, FIG. 2 shows eight large elements 36 across an elevation aperture and only one element across the lateral aperture.

The large elements 36 comprise a same or different material than the small elements 34. In one embodiment, a different piezoelectric or other material is provided for the large elements 36 than for the small elements 34. The different materials provide different electrical impedance or dielectric constant. Materials are selected such that a small element 34 has a similar or matched electrical impedance to a large element 36.

The large elements 36 are connected to the transmit beamformer 12 as transmit elements. As shown in FIG. 2, the elevation spacing of transmit elements allows steering in an elevation direction. Using a single element along the lateral aperture allows for transmission of a fan beam or uniform beam of acoustic energy within a field of view. The fan beam is parallel to the lateral dimension. By application of the transmit waveforms from the transmit beamformer to the plurality of the large elements 36, the transmit beam is originated substantially as a point source at the center of the curvature along the lateral dimension. Using the embodiment shown in FIG. 3, smaller fan beams transmitting acoustic energy uniform for ⅓ of the field of view are provided. For example, all of the larger elements 36B in the center of the rows 32 are used to generate a uniform beam of acoustic energy electrically steered in the elevation direction and transmitted into a center of the field of view.

Providing transmit waveforms to other of the larger elements 36A, 36C sequentially allows for insonnifying other regions of the field of view.

Using the transducer array 30, the transmit beamformer 12 generates a fan beam of acoustic energy uniformly covering a portion or all of a field of view along a scan plane. The transmit beamformer 12 electronically steers the fan beam in the elevation direction. Some or no electronic steering may be provided in the lateral dimension. Using the small elements 34 of the transducer array 30, the receive beamformer 18 forms a plurality of beams representing scan lines within the scan plane region uniformly insonnified by the fan beam. Data collected in response to one transmitted fan beam may be used to form a plurality or all of the receive beams along one two-dimensional plane. Alternatively, the fan beam transmission is repeated for forming additional receive beams. For the embodiment of FIG. 3, three fan beams are transmitted for each scan plane, and a plurality of receive beams associated with each of the uniformly insonnified fields of view are generated in response to each of the transmitted fan beams. Using a single transmit event and parallel receive beamforming for each of a plurality of elevationally spaced two-dimensional planes, the scan rate is increased to allow for fast three-dimensional imaging. Alternatively, non-real time three-dimensional imaging is used.

Figure 4:
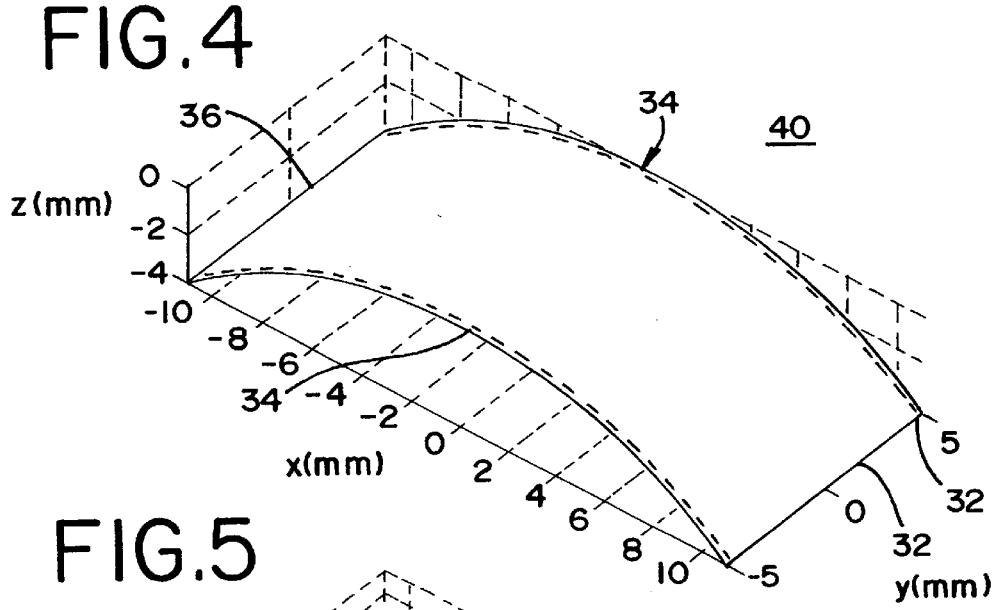

FIG. 4 shows another embodiment of an array 40 of elements 34, 36. The array is adapted for operation with a 192 system channels. Two rows 32 of small elements 34 operate as receive elements. Forty laterally spaced receive elements are provided in each of the two rows 32, providing 80 receive elements. The two rows 32 of receive elements are on opposite sides of the elevation aperture of the array 40, surrounding the rows 32 of large elements 36. The two rows 32 of receive elements are on the elevational edges of the array 40, but may be positioned elsewhere along the elevation aperture. Thirty two additional rows 32 are provided between the two rows 32 of receive elements. These thirty-two additional rows 32 each comprise one large element 36 extending across the entire lateral aperture. Thirty two transmit channels connect with the 32 large elements 36. Eighty receive channels connect with the 80 small elements 34. Using the array 40 shown in FIG. 4, direct connections are provided to the transmit beamformer 12 and receive beamformer 18 without multiplexing. Using the larger elements 36 as transmit elements allows focusing and steering in the elevation direction for transmission of a fan beam along the lateral dimension. Receive beams along lines within the scan plane are electronically focused along the lateral dimension by the receive elements. In alternative embodiments, different numbers of rows 32, small elements 34, and large elements 36 may be used in various other combinations.

Figure 5:
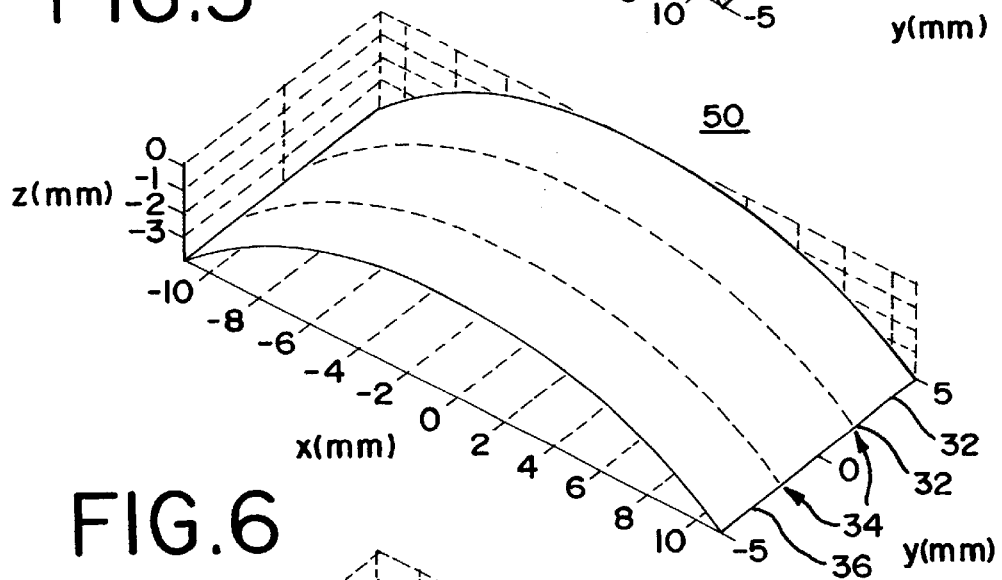

FIG. 5 shows yet another embodiment of an array 50 of elements 34, 36. The elevational pitch of the rows 32 of small elements 34 is reduced to minimize the level of side lobes as compared to the array 40 of FIG. 4. The rows 32 of small elements 34 used as receive elements are spaced from the elevation edges of the array 50. For example, ten rows 32 of large elements 36 are provided between each elevation edge and one of the rows 32 of small elements 34, but other spacings may be used. Spacing the receive elements inwards within the elevational aperture also minimizes the risk of blocking the receive elements by ribs or another opaque barrier of the patient.

Figure 6:
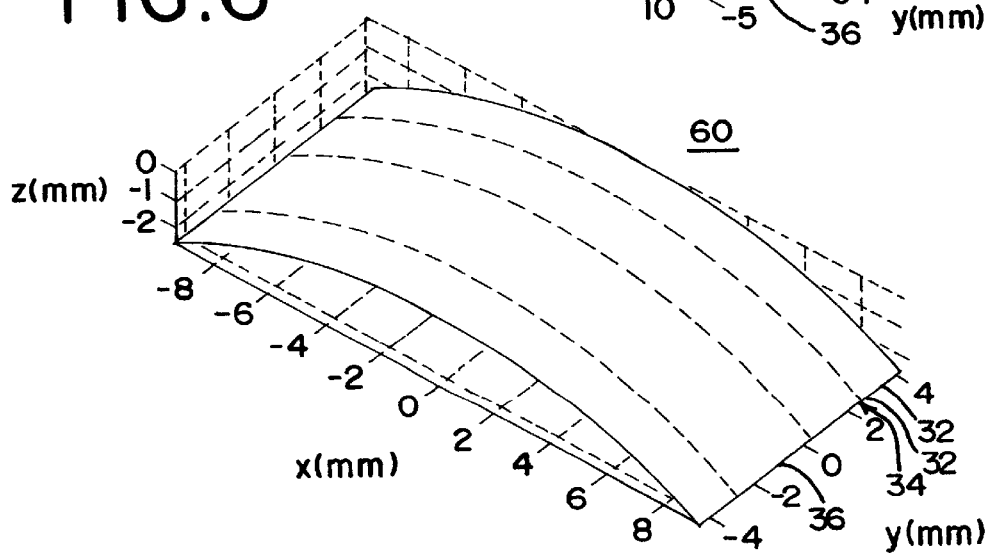

FIG. 6 shows yet another embodiment for reduction of side lobe levels associated with the two-way response.

Instead of two rows 32 of receive elements or small elements 34, three rows 32 of small elements 34 are provided. While one, two or all of the rows 32 of small elements 34 may be on an elevation edge of the array 60, the embodiment of FIG. 6 shows all of the rows 32 of receive elements spaced from the elevational edges of the array 60. The rows 32 of receive elements may be equidistant from each other or symmetrically spaced within the array 60, but are shown as having a different number of rows 32 of large elements 36 between pairs of the rows 32 of receive elements. In yet a further embodiment, a fourth row 32 of small elements 34 is provided. With 256 system channels and associated cables, each receive row 32 has sixty-four small elements 34. The sixty-four small elements 34 extend across a lateral aperture in each row 32. By electronic switching, the rows 32 of small elements 34 may be switched to operate as four single elements extending across the lateral aperture for transmitting fan beams, but may be used exclusively for reception of acoustic energy in other embodiments. With 256 cables and 256 receive elements, a high voltage multiplexer switches the cables between the receive elements and the large elements 36 for transmission. For example, high voltage multiplexers switch thirty-two of the cables to thirty-two large elements 36.

Figure 7:
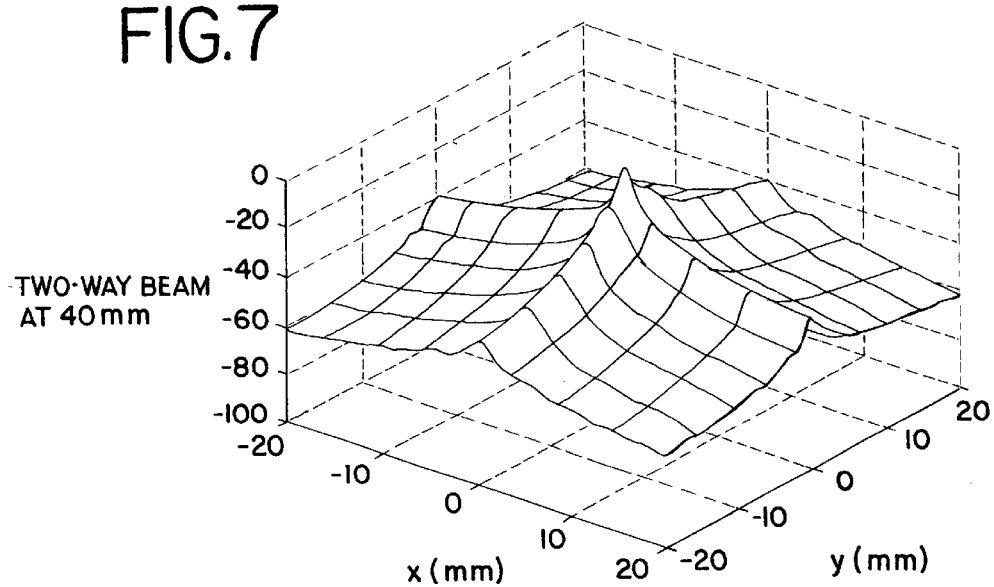
FIGS. 7–9 are graphical representations of simulations of off-focus beam profiles responsive to the transducer arrays represented in FIGS. 3–6, respectively.
Figure 8:
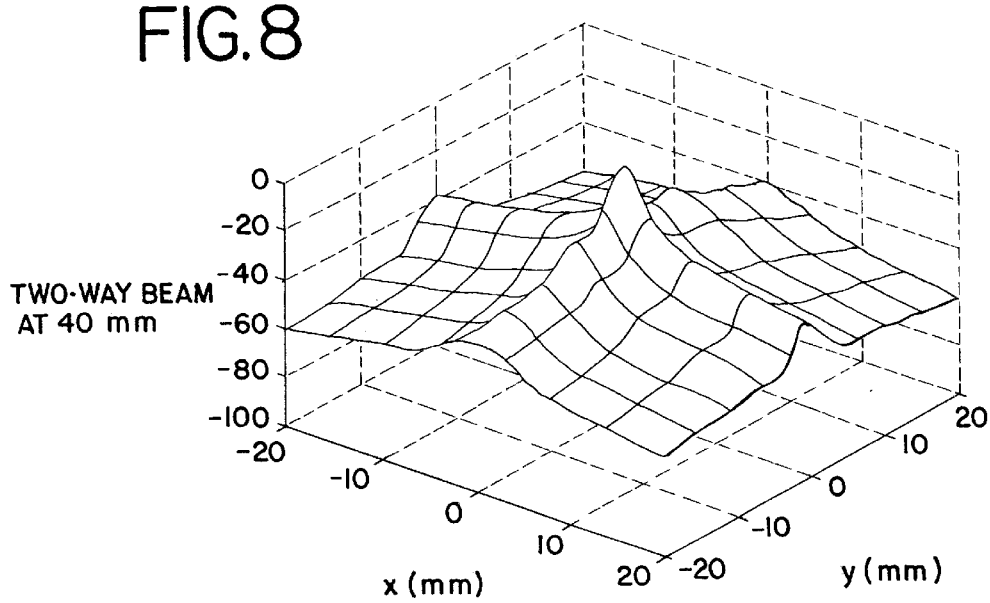
Figure 9:
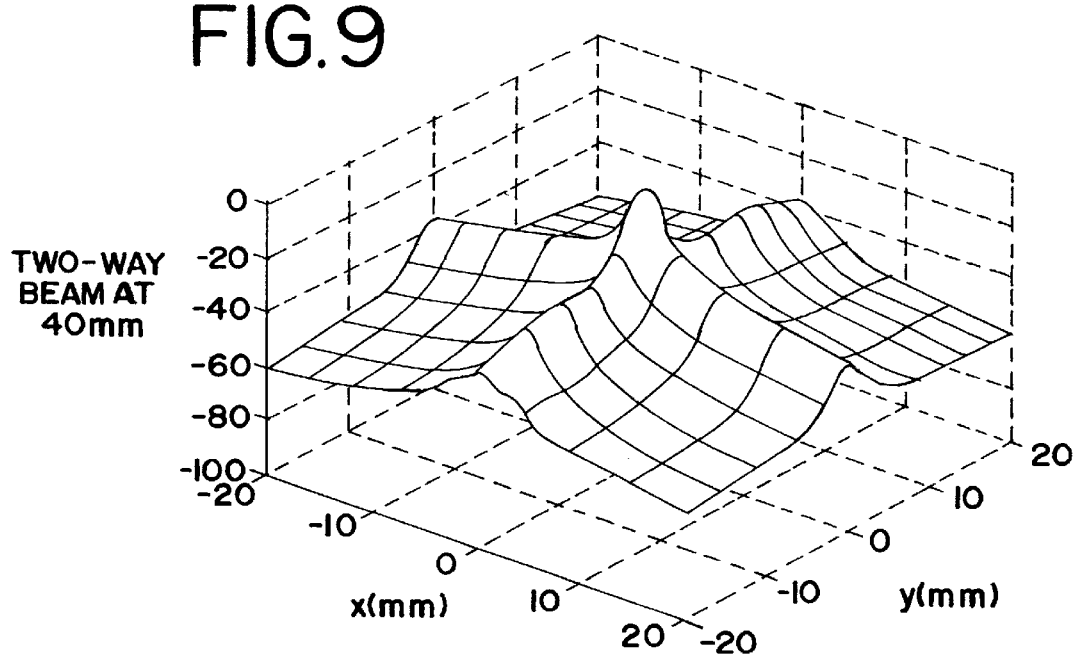

Two-way or transmit and receive response simulations of the array 40 shown in FIG. 4 indicate elevational side lobes at an approximate −12 dB point for off-focus cases, such as at a 40 millimeter distance associated with a 90 millimeter transmit focus and a 30 millimeter receive focus. Side lobes at plus or minus 2.8 $\lambda$ along the lateral dimension exist for off-focus cases, such as at a 30 millimeter distance associated with a 90 millimeter transmit focus and a 30 millimeter receive focus. A wide beam width may be provided at −12 dB or lower. FIG. 7 shows a two-dimensional beam profile associated with the array 40 of FIG. 4. The transmit focus for the simulation shown in FIG. 7 was set at 90 millimeters with a receive focus of 40 millimeters. A signal-to-clutter ratio at five wavelengths from the focal volume is 3.8 dB, and a signal-to-clutter ratio within ten wavelengths of the focal volume is 8.0 dB. Changing the position of the rows 32 of receive elements as shown in FIG. 5 results in reduced side lobe levels in 1D and 2D simulations at the off-focus distances discussed above. FIG. 8 shows a two-dimensional beam profile plot for the two-way response of the array 50 of FIG. 5. With a transmit focal point of 90 millimeters and receive focal point of 40 millimeters, the signal-to-clutter ratio within five wavelengths is 4.2 dB, and the signal-to-clutter ratio within ten wavelengths is 9.5 dB. FIG. 9 shows a two-dimensional beam profile plot of the two-way response using the array 60 of FIG. 6. With the transmit and receive focal points discussed above, the signal-to-clutter ratio within five wavelengths is 4.4 dB, and the signal-to-clutter ratio within ten wavelengths is 10.5 dB.

To improve the signal-to-noise ratio associated with limited receive and transmit apertures, pre-amplifiers may be provided for each receive element within the transducer array and housing 16 (FIG. 1). Pre-amplifiers are positioned in the probe header. The pre-amplifiers match the high impedance of the receive elements with the low electrical impedance of the coaxial cables. In one embodiment, the pre-amplifiers are programmable, but pre-amplifiers with set gains may be used.

Figure 10:
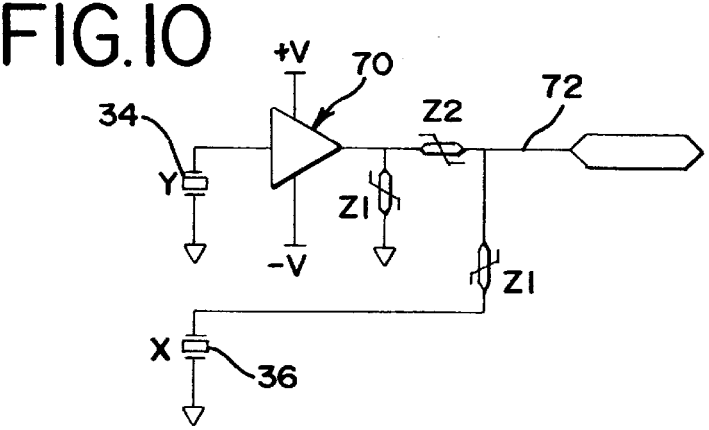
FIG. 10 is a circuit diagram of one embodiment of an amplifier with associated receive and transmit connections.

Using a transmit element separate from a receive element allows driving two array elements with one system channel. FIG. 10 shows a circuit diagram of one embodiment for connecting a single cable channel to separate transmit and receive elements. An input of an amplifier 70 connects with a small element 34 operated as a receive element. The system channel 72 connects through a nonlinear analog component network to an output of the amplifier 70. The system channel 72 also connects through a nonlinear analog component to a large element 36 for operation as a transmit element. The nonlinear components electrically isolate the small element 34 from the large element 36. For transmit, the system channel 72 provides a transmit waveform to the large element 36. For receiving acoustic energy, the receiving element drives the amplifier 70. The amplifier 70 drives the signal on the system channel 72. Any signal received by the large element 36 is minimized or comprises noise in comparison to the amplified output from the amplifier 70. Being able to connect two elements to each system channel allows for additional transmit and receive elements without requiring further system channels or high voltage multiplexers.

Figure 11:
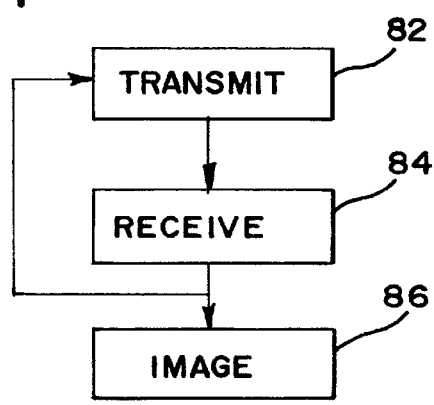
FIG. 11 is a flow chart diagram of one embodiment of a method for three-dimensional imaging with a two-dimensional transducer array.

FIG. 11 shows a flow chart of one embodiment for operation of the system 10 of FIG. 1 or another system using one of the arrays shown in FIGS. 1–6. The flow chart of FIG. 11 represents operation for three-dimensional imaging, such as real time three-dimensional imaging. In act 82, acoustic energy is transmitted. In act 84 signals are received and used to form a plurality of receive beams. Acts 82 and 84 are repeated for scanning a three-dimensional volume. In act 86, an image is rendered from the data representing three dimensions.

In act 82, a fan beam of acoustic energy is transmitted from elements that extend along a lateral aperture. For example, a uniform field of acoustic energy is transmitted over a field of view defined by transmit elements extending over the entire lateral aperture. A plurality of transmit elements are spaced along the elevation dimension. Using delays and apodization, the fan beam extending across the lateral aperture is focused in an elevation direction. Accordingly, the fan beam is transmitted within a scan plane. The fan beam has a uniform distribution of energy such that two or more, more narrow receive beams associated with lines at different lateral positions within the scan plane may be formed. In one embodiment, the uniform distribution of energy in the fan beam allows for a large number of parallel receive beams to be formed, such as tens or hundreds of receive beams formed in response to the single transmitted fan beam. The fan beam is associated with the entire laterally spacing of the region of interest or with a subsection of the entire lateral spacing, such as ⅓ of the region of interest. In alternative embodiments, the fan beam is responsive to two or more laterally spaced transmit elements.

In act 84, at least two beams are formed in response to the transmission of act 82. A plurality of laterally spaced elements and no or a fewer number of elevationally spaced rows of elements are used for receiving the acoustic energy. For example, two or more rows 32 of thirty-two or more laterally spaced elements receive echo signals in response to the transmission of a fan beam. The echo signals are delayed, apodized and summed to form data representing two or more beams within the field of view or scan plane insonnified by the fan beam. By electrical focusing in a lateral dimension, a plurality of beams representing scan lines are formed. For example, receive beam representing scan lines throughout an entire lateral extent of a region of interest are formed simultaneously. Where the transmitted fan beam uniformly insonnifies only ½, ⅓ or other lesser portion of the lateral extent of the region of interest, then receive beams representing scan lines within the insonnified region are formed. In one embodiment, four or more receive beams are simultaneously formed in response to each transmission. In yet other embodiments, tens or even hundreds of receive beams are formed in response to a single transmission using parallel beam formation and/or storage of receive signals.

Using the arrays discussed above, the receive aperture determines the lateral resolution on the azimuth or lateral dimension. The transmit aperture convolved with the separated rows of receive elements determines the elevation resolution. In alternative embodiments, only one row of receive elements is used so that the transmit aperture determines the elevation resolution. By uniformly insonnifying a large area and forming a plurality of receive beams in response, more rapid scanning of a volume is provided. Increasing the number of rows of transmit elements or receive elements may increase the elevation resolution, and increasing the number of receive or transmit elements within a row may increase the lateral resolution.

The transmit act 82 and the receive act 84 are repeated. For example, transmit act 82 is repeated to scan a different scan plane, such as an elevationally spaced scan plane. As another example, a subsequent fan beam is transmitted within a same scan plane but at a different lateral position to complete scanning of a region of interest within the scan plane. As yet another example, the transmit act 82 is repeated at a same location within a same scan plane to allow additional simultaneous beam formation of receive signals for scan lines different than previously formed. By subdividing the lateral transmit aperture into 4, 8 or more elements for transmitting fan beams, the image clutter is reduced. Resolution may be further increased by using various of the elements for both transmit and receive operations.

In act 86, an image is rendered from the beams representing a three-dimensional volume. The spatial positions represented by each of the datum are coordinated. The electrical elevation focusing and electrical lateral focusing provides the spatial location associated with the data. Once aligned, any of various rendering techniques now known or later developed are used to generate an image from the data. The images are generated in real time, such as 20 or more images generated a second. Transmission of a fan beam of uniform acoustic energy and parallel receive beam formation allow for rapid scanning of a volume of interest. A whole frame or a large portion of a frame or two-dimensional region is insonnified in one transmit event using large elements, and small elements spaced along a different dimension allow for a fair quality of a beam forming.

The array 30 may be used for two-dimensional imaging without subdivision of the large elements. The larger elements 36 or small elements 34 are used to transmit acoustic energy within a plane. The transmission may be of beams or a fan beam. The small elements 34 receive echo signals for forming beams within the plane.

While the invention has been described above by reference to various embodiments, it should be understood that many changes and modifications can be made without departing from the scope of the invention. For example, transmit and/or receive elements are positioned along different dimensions (e.g. rows 32 extending along an elevation dimension). It is therefore intended that the foregoing detailed description be understood as an illustration of the presently preferred embodiments of the invention, and not as a definition of the invention. It is only the following claims, including all equivalents, that are intended to define the scope of this invention.

What is claimed is:

1. A two dimensional array for three dimensional imaging, the array comprising:
    a first row of the array having at least one first element; and
    a second row of the array adjacent to the first row;
    wherein the second row has at least two second elements, the first element at least about twice as long along the first row as one of the second elements along the second row.

2. The array of claim 1 wherein the first and second rows are parallel.

3. The array of claim 1 wherein the first element comprises a length that is the lateral aperture size of the array and the second row comprises at least sixteen second elements within the lateral aperture size.

4. The array of claim 1 wherein the first row comprises two first elements, each first element comprising a length that is about one half the lateral aperture size of the array and the second row comprises at least sixteen second elements within the lateral aperture size.

5. The array of claim 1 wherein the first row comprises three first elements, each first element comprising a length that is about one third the lateral aperture size of the array and the second row comprises at least sixteen second elements within the lateral aperture size.

6. The array of claim 1 wherein the first element has a lateral length substantially the same as a lateral length of all of the second elements in combination.

7. A two dimensional array for three dimensional imaging, the array comprising:
    a first row having at least one first element;
    a second row adjacent to the first row;
    wherein the second row has at least two second elements, the first element at least about twice as long along the first row as one of the second elements along the second row; and
    at least a third row of at least one third element, the third element at least about twice as long as one of the second elements.

8. The array of claim 7 wherein the array comprises at least sixteen rows of the first elements.

9. The array of claim 8 wherein the array comprises at least two rows of the second elements.

10. The array of claim 9 wherein the at least two rows of the second elements are positioned on opposite sides of the at least sixteen rows of the first elements.

11. The array of claim 9 wherein the at least two rows of the second elements are spaced apart by the first row and spaced from each elevation edge of the array by at least one additional row of first elements.

12. The array of claim 1 comprising the second, a third and a fourth rows of the second elements, the second and third rows spaced apart in elevation by a first number of rows of the first elements and the third and fourth rows spaced apart in elevation by a second number of rows of the first elements, the second number of rows different than the first number.

13. The array of claim 1 wherein the first elements are connectable to receive transmit waveforms and the second elements are connectable to pass received signals in response to transmission from the first elements.

14. The array of claim 1 further comprising amplifiers connected with the second elements, the amplifiers and the array in a probe housing.

15. The array of claim 1 wherein the first element comprises a first material having a different electrical impedance than a second material of the second elements.

16. An ultrasound system for three-dimensional scanning, the system comprising:
    a transmit beamformer;
    a receive beamformer; and
    a two-dimensional array of elements, at least a first sub-set of the elements connectable with the transmit beamformer, at least a second sub-set of the elements connectable with the receive beamformer, the first sub-set of elements comprising a greater number of elevation spaced elements than lateral spaced elements, the second sub-set of elements comprising a greater number of lateral spaced elements than elevation spaced elements.

17. The system of claim 16 wherein the first sub-set of elements comprises at least sixteen elevation spaced rows of elements and the second sub-set of elements comprises fewer than nine elevation spaced rows of elements.

18. The system of claim 16 wherein the second sub-set of elements comprises a second row of at least sixteen lateral spaced elements and the first sub-set of elements comprises a first row of fewer than nine lateral spaced elements.

19. The system of claim 16 wherein the first sub-set of elements comprises at least sixteen elevation spaced rows of fewer than nine lateral spaced elements each and the second sub-set of elements comprises fewer than nine elevation spaced rows of elements, each of the fewer than nine elevation spaced rows of elements having at least sixteen lateral spaced elements.

20. The system of claim 16 wherein the two-dimensional array comprises a two-dimensional array being curved along a lateral dimension.

21. The system of claim 16 wherein each of the elements of the first sub-set of elements are at least about twice as long in a lateral dimension as each of the elements of the second sub-set of elements in the lateral dimension.

22. A method for three-dimensional scanning with a two-dimensional array, the method comprising:
    (a) transmitting acoustic energy electronically focused in an elevation dimension, the acoustic energy having a uniform field in a lateral dimension; and
    (b) forming at least two beams electrically focused in the lateral dimension in response to (a).

23. The method of claim 22 wherein (a) comprises transmitting from an array of elements spaced along an elevation dimension and each having a lateral dimension at least one eighth of a lateral aperture, and wherein (b) comprises forming in response to at least sixteen elements spaced in a row within the lateral aperture.

24. The method of claim 22 wherein (a) comprises transmitting a fan beam of acoustic energy.

25. The method of claim 24 wherein (a) comprises transmitting in a first scan plane and (b) comprises forming at least a third of a total number of laterally spaced receive beams in the first scan plane in response to (a); and further comprising:
    (c) transmitting acoustic energy electronically focused in a second scan plane, the second scan plane spaced in elevation from the first scan plane; and
    (d) forming at least a third of a total number of laterally spaced receive beams in the second scan plane in response to (c).

26. The method of claim 22 further comprising:
    (c) generating an image in response to (c);
    wherein a lateral resolution is a function of only a receive aperture and the elevation resolution is a function of a transmit aperture convolved with a receive aperture.

27. The method of claim 22 wherein (b) comprises forming the at least four beams substantially simultaneously.

28. The method of claim 22 further comprising:
    (c) generating a two-dimensional representation as a function of the at least two beams.

* * * * *